US008679851B2

(12) United States Patent
Fang et al.

(10) Patent No.: US 8,679,851 B2
(45) Date of Patent: Mar. 25, 2014

(54) METHOD FOR DETERMINING TURBIDITY POINT AND FREE CARBOHYDRATE BUFFER COEFFICIENT OF IRON-CARBOHYDRATE COMPLEX

(75) Inventors: Wen Fang, Jiangsu (CN); Chuanzheng Hua, Jiangsu (CN); Jie Yang, Jiangsu (CN); Guoxin He, Jiangsu (CN); Shoujun Xiong, Jiangsu (CN)

(73) Assignee: Nanjing Lifenergy R&D Co., Ltd, Nanjing, Jiangsu (CN)

( * ) Notice: Subject to any disclaimer, the term of this patent is extended or adjusted under 35 U.S.C. 154(b) by 0 days.

(21) Appl. No.: 13/515,162

(22) PCT Filed: Jan. 13, 2010

(86) PCT No.: PCT/CN2010/070165
§ 371 (c)(1),
(2), (4) Date: Jun. 11, 2012

(87) PCT Pub. No.: WO2011/069347
PCT Pub. Date: Jun. 16, 2011

(65) Prior Publication Data
US 2012/0276650 A1    Nov. 1, 2012

(30) Foreign Application Priority Data

Dec. 9, 2009 (CN) .......................... 2009 1 0232202

(51) Int. Cl.
*G01N 21/47* (2006.01)
*G01N 21/01* (2006.01)
*G01N 21/00* (2006.01)

(52) U.S. Cl.
USPC ................. 436/127; 702/25; 702/23; 702/22; 702/1

(58) Field of Classification Search
USPC ............................ 436/127; 702/25, 23, 22, 1
See application file for complete search history.

(56) References Cited

FOREIGN PATENT DOCUMENTS

| CN | 1905905 A | 1/2007 |
| GB | 1122809 A | 8/1968 |
| WO | 2007076117 A2 | 7/2007 |
| WO | 2008140874 A1 | 11/2008 |

*Primary Examiner* — Christine T Mui
(74) *Attorney, Agent, or Firm* — Morris Manning & Martin LLP; Tim Tingkang Xia, Esq.

(57) ABSTRACT

A method for determining a turbidity point and a free carbohydrate buffer coefficient of an iron-carbohydrate complex. The method includes: (1) contacting the complex with an acid; (2) determining hydrogen ion concentrations and solution turbidities of the complex in acid degradation; and (3) mathematically fitting the data, to obtain the turbidity point of the complex and the free carbohydrate buffer coefficient through mathematical treatment. A method for evaluating the safety of the iron-carbohydrate complex with the turbidity point and the free carbohydrate buffer coefficient.

14 Claims, 3 Drawing Sheets

METHOD FOR DETERMINING TURBIDITY POINT AND FREE CARBOHYDRATE BUFFER COEFFICIENT OF IRON-CARBOHYDRATE COMPLEX

FIELD OF INVENTION

The present invention relates to the field of macro-molecule analysis and determination, and in particular, to a method for determining turbidity point and free carbohydrate buffer coefficient of an iron-carbohydrate complex.

RELATED ART

Iron is an essential trace element in human body, but iron deficiency caused by insufficient intake, limited availability, or other reasons is quite prevalent, and iron deficiency anemia (IDA) is the nutrient deficiency disease most widely distributed in the world currently. Iron-carbohydrate complexes are iron supplement against IDA that are widely used presently, especially in IDA caused by haemodialysis in treatment of kidney diseases, and have the advantages of fast acting, high efficiency, accurate targeting, and low risk.

The iron-carbohydrate complexes are obtained by complexing carbohydrate with polynuclear ferric hydroxide colloid. The iron nucleus is located at the core position, and the carbohydrate is located at an outer layer of the molecule, thus forming a concentric spherical structure. The main difference of different species of iron-carbohydrate complexes lies in that the species of the carbohydrate is different or the molecular weight is different. For example, iron sucrose is a water soluble ferric hydroxide-sucrose complex prepared by complexing the ferric hydroxide colloid with sucrose, in which iron is in a non-ion state. In the molecule, the ferric hydroxide colloid forms a polynuclear iron parent core, sucrose is bound to the iron parent core by replacing water molecules on the surface thereof with the active hydroxyl groups, and the binding force therebetween is non-covalent intermolecular force. In iron sucrose, sucrose serves as a solubilizing agent of the ferric hydroxide colloid, and a dynamic equilibrium exists between sucrose and the ferric hydroxide colloid. The polynuclear ferric hydroxide core is shallowly surrounded by a large amount of sucrose molecules bound with non-covalent bonds thereto, thus forming a macro-molecule complex of about 43 Kda. The polynuclear iron complex has a structure similar to that of naturally occurring ferritin, and has suitable stability, thus ensuring that no iron ion is released under physiological conditions, and being suitable for physiological absorption and utilization of iron.

Researchers have made some useful attempts on the safety evaluation of an iron-carbohydrate complex. Dr. Nissim associated the safety of an iron sucrose complex (quantitatively evaluated with survival rate of test animal in acute toxicity test) with the turbidity point thereof in "Preparation and Standardisation of Saccharated Iron Oxide for Intravenous Adminstration" (The Lancet. Apr. 23, 1949. (686-689)), and found that the safety and the turbidity point have a correlation that at the same dose, the survival rate of the test animal rises with the drop of the turbidity point, and a certain semi-logarithmic linear relation is exhibited. It is suggested by researchers that, the turbidity point of the iron sucrose complex can indicate the safety level of iron sucrose, which is obviously correlated to the in vivo stability of the iron sucrose complex in the physiological environment in an animal body. However, unfortunately, Dr. Nissim did not further study the physical meanings and determination method of the turbidity point. In literatures, Dr. Nissim did not give a strict definition of the turbidity point, and the determination method is to add hydrochloric acid dropwise and visually observe the changes of the solution turbidity with naked eyes. The author did not mention and study in detail the acid degradation kinetics of iron sucrose and the relation between the acid degradation kinetics and the turbidity point, and did not establish a definite relation between the acid degradation kinetics and safety of iron sucrose, either.

Over the years, the researches in this field are still at a standstill, and the only researches are limited to the definition and optimization of the observation conditions in the method for determining the turbidity point. For example, it is specified in United States Pharmacopeia that the turbidity point of the iron sucrose injection should be controlled in the range of 4.4-5.3. However, unfortunately, although the method for determining the turbidity point of the iron sucrose injection in United States Pharmacopeia is more advanced than that of Dr. Nissim, the method is still to determine the turbidity point by visually observing the turbidity with naked eyes. The determination method in United States Pharmacopeia includes: formulating an iron sucrose solution of a certain concentration in a transparent vessel; allowing parallel light to pass through the iron sucrose solution in the vessel in a dark room; dropping a hydrochloric acid solution slowly with continuous stirring, till the solution in the light path begins to become turbid; and recording the corresponding pH value as the turbidity point. In such a method, the turbidity is also determined with naked eyes absolutely, such that the subjectivity is strong, and the result is easily influenced by the operation conditions, test environments, and the intensity of the light source used, and thus different results are obtained for the same sample when being tested by different persons; and even when being tested by the same person, the test results may be different under different test conditions. Over the years, such a method is continuously used without improvements, and in the new edited United States Pharmacopeia (USP32), the method is still used to determine the turbidity point of the iron sucrose injection.

It is a useful trial for solving the problem that the subjectivity in determining of the turbidity point by visually observing is too strong, to directly determine the turbidity of an iron sucrose solution with a turbidimeter, and determine the turbidity point by determining the pH value of the iron sucrose solution with a designated turbidity value. However, according to the definition of the turbidity point of the iron sucrose solution, the solution turbidity of the iron sucrose solution is still very low at the turbidity point pH value. The accurate measurement of low turbidity will pose high requirements on the precision of the turbidimeter, and common turbidimeters cannot meet the requirements. Furthermore, it cannot be avoided that the test solution always has an unstable background turbidity, which will interfere the determination with the turbidimeter. As a result, even if the turbidimeter has a high precision, it still cannot determine the real turbidity and turbidity changes of the solution, and thus has difficulty to determine the corresponding turbidity point. Therefore, at present, there is no report about determination of the turbidity point of iron sucrose by using the method.

SUMMARY OF THE INVENTION

In view of the disadvantages in determination of turbidity point of an iron-carbohydrate complex in the prior art of strong subjectivity, being easily influenced by operation conditions and test environment, and high test error of the turbidity analyzer at a low measurement range, the present invention is directed to a method for accurately determining a turbidity and a free carbohydrate buffer coefficient through turbidity determination with an instrument in combination with data fitting.

The present invention is further directed to a use of the determination method in safety evaluation of an iron-carbohydrate complex.

The objectives of the present invention are achieved through the following measures.

The terms involved in the present invention are defined as follows.

Turbidity point (pp): in a solution of an iron-carbohydrate complex such as iron sucrose complex, pH value at which the solution turbidity caused by increasing number of insoluble molecules reaches a certain critical value (the solution begins to become turbid), with the decrease of pH value of the solution and gradual accumulation of insoluble molecules, is called as the turbidity point of a solution of an iron-carbohydrate complex such as iron sucrose.

Free carbohydrate buffer coefficient (n): in a solution of an iron-carbohydrate complex such as iron sucrose, the number of sucrose molecules lost during the formation of insoluble molecules due to the attack of hydrogen ions is called as free carbohydrate buffer coefficient, which represents the buffering capability of an iron-carbohydrate complex such as iron sucrose for resisting the attack of hydrogen ions, and also reflects the buffering capability of the iron-carbohydrate complex such as iron sucrose in conversion from a soluble non-toxic substance into an insoluble toxic molecule.

It is found through researches on acid degradation kinetics of an iron-carbohydrate complex such as iron sucrose that, at different pH values, a strict function quantitative relation exists between the turbidity of the solution of the iron-carbohydrate complex and the concentration of hydrogen ions in the solution; and the function equation can be determined by determining the corresponding relation between hydrogen ions and the solution turbidities at finite points, so as to theoretically calculate the turbidity point and free carbohydrate buffer coefficient of the iron-carbohydrate complex.

Principle of Acid Degradation Kinetics of Iron-Carbohydrate Complex such as Iron Sucrose It is found through researches that in an aqueous solution environment, the acid degradation of the iron-carbohydrate complex satisfies a specific kinetic rule, for example, the acid degradation of iron sucrose complex satisfies the following rules.

The reaction process includes:

(1) $I + H^+ \rightleftharpoons I_1 + G$   $k1 = [I_1][G]/[I][H^+]$
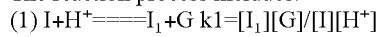
(2) $I_1 + H^+ \rightleftharpoons I_2 + G$   $k2 = [I_2][G]/[I_1][H^+]$
...

(n) $I_{n-1} + H^+ \rightleftharpoons I_n + G$   $kn = [I_n][G]/[I_{n-1}][H^+]$ if $K' = k_1 k_2 k_3 k_n$ $K' = ([I_1][G]/[I][H^+])*([I_2][G]/[I_1][H^+]) \ldots *([I_n][G]/[I_{n-1}][H^+])$

$= [G]^n[I_n]/[I][H^+]^n$ (a)

in which 1) reactions in Step 1 to Step n−1 are rapid equilibrium, reaction in Step n is a control step, and $k_1$, $k_2$, $k_3$, and $k_n$ are reaction equilibrium constants of the unit reaction steps;

2) the water solubility of the degradation product $I_n$ generated after n sucrose molecules are removed from I is sharply decreased, and thus turbidness of the solution occurs, which underlies the increase of the solution turbidity and the toxicity of the iron-carbohydrate complex such as iron sucrose;

3) during the reaction, compared with the change in the concentration of $H^+$, the concentration of free sucrose is not changed much and thus considered as a constant concentration; and [I] is a constant;

4) the concentration of $I_n$ is in direct proportion to the solution turbidity, that is, $[I_n] = kN$, in which k is a proportionality coefficient;

5) G represents a sucrose molecule, I represents an iron sucrose molecule, $I_n$ represents a product generated after the iron sucrose molecule is reacted with n hydrogen ions, to remove n sucrose molecules; and 6) [ ] represents concentration.

Based on the above, if $K'[I]/[G]^n k = K$, Equation (a) is changed to be:

$K'[I]/[G]^n k = N/[H^+]^n$

That is, $K = N/[H^+]^n$ (b)

Logarithms of both sides of Equation (b) are taken with the same base, and $\log_m K = \log_m N - n\log_m[H^+]$, so $\log_m N = n\log_m[H^+] + \log_m K$.

The function relation is linearized, where if $\log_m N = y$, and $\log_m[H^+] = x$, $y = nx + \log_m K$ (C1).

Thus, the coefficient n and $\log_m K$ of Equation (C1) can be fitted by determining a few values of N and $[H^+]$.

For ease of examination and calculation, preferably, logarithms of both sides of Equation (b) are taken with 10 as the base, and $\lg K = \lg N - n\lg[H^+]$ is obtained, so $\lg N = -n pH + \lg K$.

The function relation is linearized, where if $\lg N = y$, and $pH = x$, $y = -nx + \lg K$ (C2).

Thus, the coefficient n and $\log K$ of Equation (C2) can be fitted by determining a few values of N and a few pH values.

Obviously, the coefficient n in Equations (C1) and (C2) represents the following physical meaning The number of the sucrose molecules lost during the formation of insoluble molecules when the iron sucrose molecules in the solution are attacked by hydrogen ions is called as free sucrose buffer coefficient, which represents the buffering capability of iron sucrose for resisting the attack of hydrogen ions, and also reflects the buffering capability of iron sucrose in conversion from a soluble non-toxic substance into an insoluble toxic molecule, and correlates to the safety of iron sucrose.

Moreover, in addition of an acid, the insoluble molecules are gradually accumulated in the solution of iron sucrose. According to the determination method of the United States Pharmacopeia, a critical pH value at which the solution turbidity caused by accumulation of insoluble molecules is increased to such an extent that a tester can observe the turbid phenomenon under a certain light intensity is called as the turbidity point of the iron sucrose solution. In fact, the critical pH value can be accurately obtained through a mathematical method. The turbidity visible to naked eyes under the test conditions is quantified, and is introduced into the curve fitting Equation (C1) or (C2), to obtain the accurate value of the turbidity point through equation solving, referring to FIG. 1. In addition, in view of the difference in distinguishing capability of naked eyes of different people, and the high test error of the turbidity analyzer at a low measurement range, a straight line with a certain slope may be further used. The straight line is made to be tangent to a target curve, to obtain the position of a tangent point. The abscissa corresponding to the tangent point is the accurate value of the turbidity point, and the solution method is as shown in FIG. 2.

Furthermore, the pH values during the test and the corresponding turbidities of the iron sucrose solution are determined with instruments respectively, and are fitted according to the reaction mechanism with a computer system, thus the turbidity point of the iron sucrose solution can be rapidly determined in no more than 5 min generally. The method is rapid and accurate, and is applicable in safety evaluation of iron sucrose, as well as in control of complex reaction during the preparation of the raw material of iron sucrose.

Based on this, it is also found through researches that the safety and stability of iron sucrose under physiological conditions directly correlates to the acid degradation kinetics, that is, the turbidity point, as well as the free sucrose buffer coefficient in aqueous solution, but not the turbidity point obtained through the acid degradation kinetics alone.

The present invention provides a method for determining the turbidity point and the free carbohydrate buffer coefficient of an iron-carbohydrate complex, which includes:

(1) contacting the complex with an acid;
(2) determining the hydrogen ion concentration and the solution turbidity in acid degradation of the complex; and
(3) mathematically fitting the data, to obtain the turbidity point and the free carbohydrate buffer coefficient of the iron-carbohydrate complex through mathematical treatment.

Preferably, the method for determining the turbidity point and the free carbohydrate buffer coefficient includes:

(1) contacting the iron-carbohydrate complex with an acid;
(2) determining the hydrogen ion concentrations and solution turbidities N at finite points with a pH meter and a turbidimeter; and
(3) introducing the determined turbidity value and the hydrogen ion concentration in the equation $K=N/[H^+]^n$, and taking logarithms of both sides of the equation with the same base, to obtain all the coefficients in the fitted equation $\log_m N = n \log_m [H^+] + \log_m K$, including the free carbohydrate buffer coefficient n of the iron-carbohydrate complex; and treating the fitted equation with a secant method or a tangent method, to obtain the turbidity point of the iron-carbohydrate complex.

Particularly preferably, the method for determining the turbidity point and the free carbohydrate buffer coefficient includes:

(1) contacting the iron-carbohydrate complex with an acid;
(2) determining the hydrogen ion concentrations and the solution turbidities N at finite points with a pH meter and a turbidimeter; and
(3) taking the logarithms of the determined turbidity values with a base of 10, and performing least square fitting on the log values and the corresponding pH values, to obtain all the coefficients in the fitted equation $\lg N = -npH + \lg K$, including the free carbohydrate buffer coefficient n of the iron-carbohydrate complex; and treating the fitted equation with a secant method or a tangent method, to obtain the turbidity point of the iron-carbohydrate complex.

As for the tangent method, different tangent slopes in a tangent slope range from −30 to 0, and preferably from −20 to −5 can be selected.

As for the secant method, different secant iteration distances in an iteration distance range such that the turbidity of the solution is higher than 0 and lower than 5, and preferably higher than 0.5 and lower than 3 can be selected.

The carbohydrate in the iron-carbohydrate complex is at least one selected from dextran, dextrin, gluconate, sorbitol, or sucrose, with sucrose being preferred.

The acid is at least one selected from hydrochloric acid, sulfuric acid, nitric acid, perchloric acid, hydrobromic acid, hydroiodic acid, hyperbromic acid, chloric acid, bromic acid, permanganic acid, hydroboric acid, fluorosulfonic acid, cyanic acid, thiocyanic acid, trifluoroacetic acid, trichloroacetic acid, methanesulfonic acid, benzenesulfonic acid, oxalic acid, and formic acid, with hydrochloric acid being preferred.

The present invention further provides a use of the method for determining the turbidity point and the free carbohydrate buffer coefficient of the iron-carbohydrate complex in safety evaluation of an iron-carbohydrate complex.

A method for evaluating the safety of an iron-carbohydrate complex includes:

(1) contacting the iron-carbohydrate complex with an acid;
(2) determining the hydrogen ion concentrations and the solution turbidities N at finite points with a pH meter and a turbidimeter; and
(3) introducing the determined turbidity value and the hydrogen ion concentration into the equation $K=N/[H^+]^n$, taking the logarithms of both sides of the equation with the same base, to obtain all the coefficients in the fitted equation $\log_m N = n \log_m [H^+] + \log_m K$, including the free carbohydrate buffer coefficient n of the iron-carbohydrate complex; and treating the fitted equation with a secant method or a tangent method, to obtain the turbidity point of the iron-carbohydrate complex.

If the obtained turbidity point is in the range of 4.4-5.3, and the obtained free carbohydrate buffer coefficient n is higher than 2.5, it is indicated that the iron-carbohydrate complex has good safety.

Preferably, the method for evaluating the safety of the iron-carbohydrate complex includes:

(1) contacting the iron-carbohydrate complex with an acid;
(2) determining the pH values and the solution turbidities at finite points with a pH meter and a turbidimeter; and
(3) taking the logarithms of the determined turbidity values with a base of 10, and performing least square fitting on the log values and the corresponding pH values, to obtain all the coefficients in the fitted equation $\lg N = -npH + \lg K$, including the free carbohydrate buffer coefficient n of the iron-carbohydrate complex; and treating the fitted equation with a secant method or a tangent method, to obtain the turbidity point of the iron-carbohydrate complex.

If the obtained turbidity point is in the range of 4.4-5.3, and the obtained free carbohydrate buffer coefficient n is higher than 2.5, it is indicated that the iron-carbohydrate complex has good safety.

As for the tangent method, different tangent slopes in a tangent slope range from −30 to 0, and preferably from −20 to −5 can be selected.

As for the secant method, different secant iteration distances in an iteration distance range such that that the turbidity of the solution is higher than 0 and lower than 5, and preferably higher than 0.5 and lower than 3 can be selected.

The present invention provides a quality control device for evaluating the safety of an iron-carbohydrate complex. The device includes the following main modules: a solution turbidity tester, a solution hydrogen ion concentration tester, a vessel for containing the iron-carbohydrate complex and a stirrer, a vessel for containing the acid solution and a dropping device, a device for reading the turbidity and the hydrogen ion concentration, and a mathematical simulation module of acid degradation kinetics of the complex and a result output device.

The present invention provides a control method for distinguishing the quality of different batches of iron-carbohydrate complexes with substantially similar degradation kinetics using the method for determining the turbidity point and the free carbohydrate buffer coefficient of the iron-carbohydrate complex, which includes:

(1) determining the turbidity points and the free carbohydrate buffer coefficients of the iron-carbohydrate complexes of the batches to be tested; and
(2) distinguishing the batch of the iron-carbohydrate complex with the same turbidity point and free carbohydrate buffer coefficient as those of a standard composition.

The present invention has the following benefit effects.

The present invention firstly provides a method for determining the turbidity point of the iron-carbohydrate complex in a strict sense through mathematical fitting of the hydrogen ion concentrations and the corresponding turbidities at finite points of the iron-carbohydrate complex solution determined with an instrument, and extrapolation, so as to avoid the influence on the determination result of the subjectivity of the operator and the test environment, and ensure the repeatability and accuracy of the determination result. As the turbidity point value is a critical pH value at which the solution of the iron-carbohydrate complex begins to get turbid, the turbidity is very low. The test error of the current turbidity determination instrument at a low measurement range is high, and thus the turbidity point cannot be easily determined. In the present invention, the turbidity of a relatively high value and the corresponding hydrogen ion concentration are determined with an instrument, and the turbidity point is obtained through extrapolation according to the function relation thereof, to avoid determining of the iron-carbohydrate complex at a low turbidity with a turbidimeter, so as to ensure the accuracy of turbidity determination, avoid the strict requirements for the precision of the turbidimeter, and obtain the free carbohydrate buffer coefficient n at the same time, and thus the determination method of the present invention is very important for improving the control level and safety of the iron-carbohydrate complex.

Based on the finding that the safety of an iron-carbohydrate complex correlates to the turbidity point pp and the free carbohydrate buffer coefficient n of the solution thereof, the present invention establishes a method for evaluating the safety of the iron-carbohydrate complex, and firstly proposes PP (turbidity point) and n (free carbohydrate buffer coefficient) of iron-carbohydrate complex in the strict sense as the indicator for evaluating the quality and safety of the iron-carbohydrate complex, and defines a determination range of PP (4.4-5.3), and n (n>2.5) in which the iron-carbohydrate complex is safe. The two parameters have different meanings in evaluation of the safety of iron sucrose complex, in which the turbidity point reflects the critical pH value at which an insoluble ingredient of iron sucrose is generated, and the free carbohydrate buffer coefficient reflects the buffering capability of the iron sucrose complex in conversion from a soluble ingredient into an insoluble ingredient.

DETAILED DESCRIPTION OF THE INVENTION

Embodiment 1 Method for Determining the Turbidity Point (PP) and Free Sucrose Buffer Coefficient (n) of Iron Sucrose Preparation of test solution of iron sucrose: 1 g iron sucrose injection is placed in a 300 ml beaker, and diluted with 200 ml water, to obtain the solution.

Preparation of acid solution: a 0.1 mol/L hydrochloric acid solution is made with concentrated hydrochloric acid by adding purified water. 0.1 mol/L hydrochloric acid solution is added dropwise into the test solution of iron sucrose with continuous stirring. The solution turbidities are determined with a turbidimeter respectively at different pH values, and the pH value and the turbidity data are recorded.

TABLE 1

Original data of acid degradation kinetics of iron sucrose

| | pH | | | | | |
|---|---|---|---|---|---|---|
| | 4.65 | 4.55 | 4.46 | 4.34 | 4.23 | 4.16 |
| N | 0.583 | 1.364 | 5.41 | 8.68 | 35.28 | 61.66 |
| lgN | −0.2343 | 0.1348 | 0.7332 | 0.9385 | 1.5475 | 1.7900 |

Figure 1:
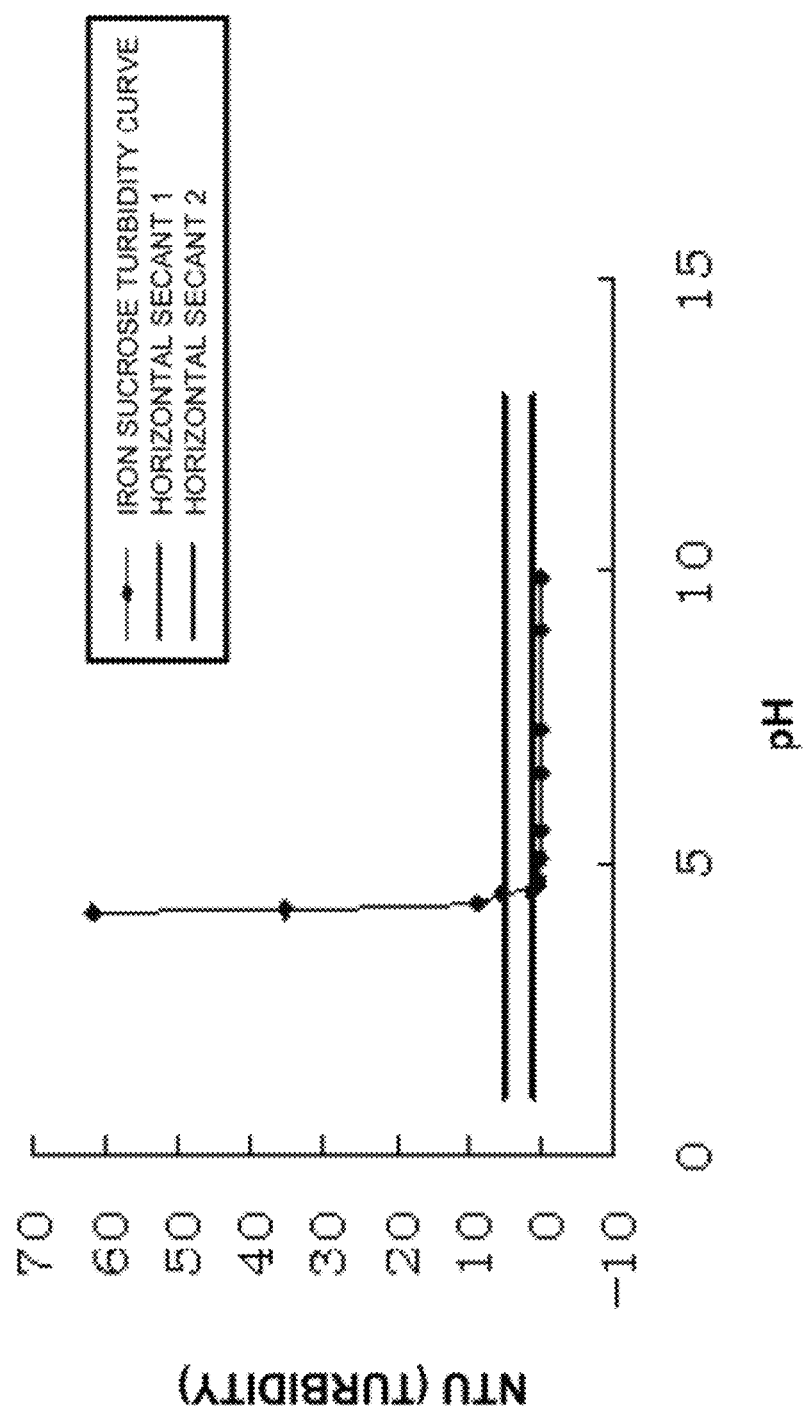
FIG. 1 is a diagram illustrating a principle of calculating the turbidity point of iron sucrose with a secant method.
Figure 2:
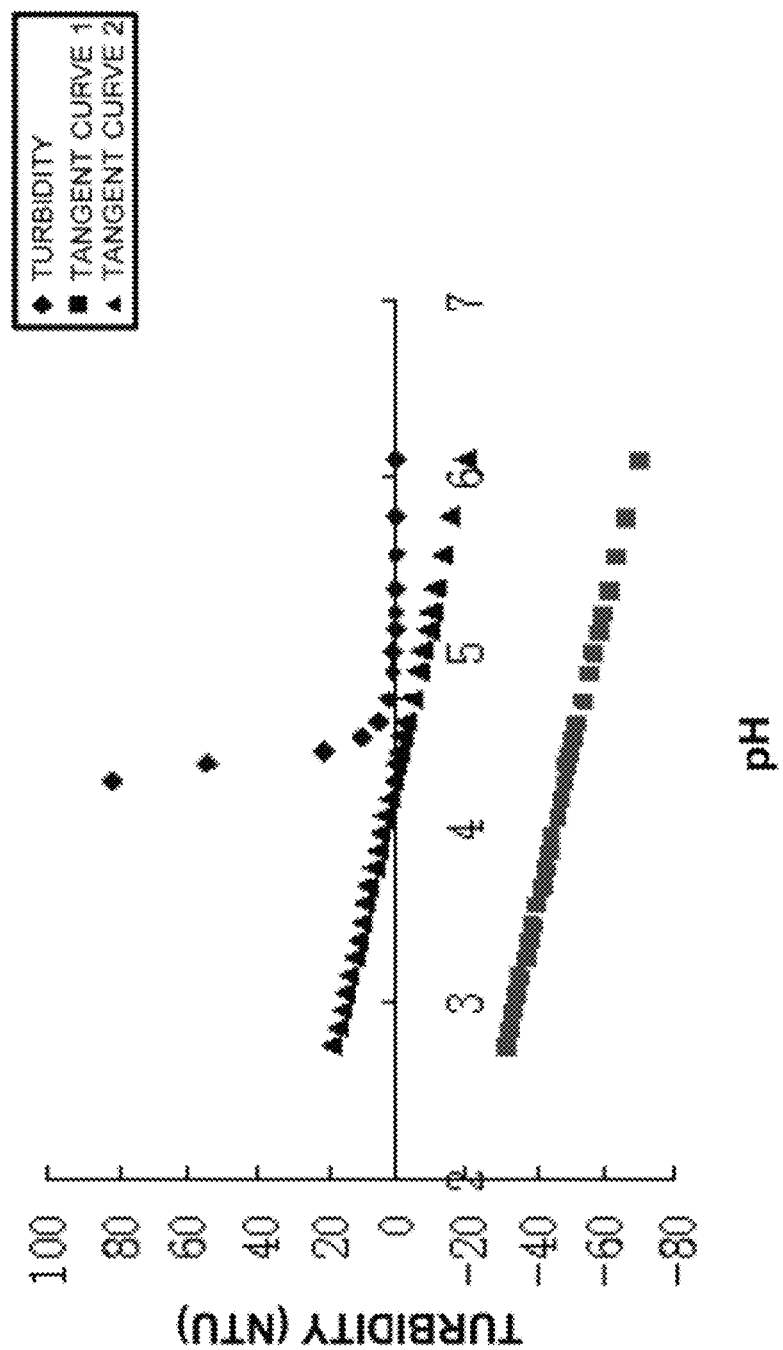
FIG. 2 is a diagram illustrating a principle of calculating the turbidity point of iron sucrose with a tangent method.
Figure 3B:
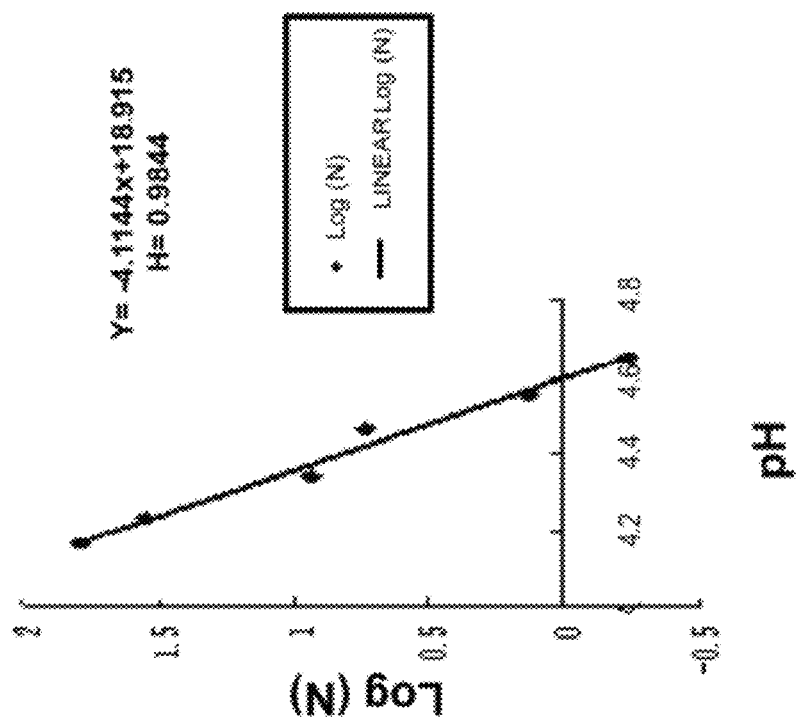
FIG. 3 shows a relation fitting curve of the turbidity of iron sucrose and the pH value, in which FIG.(a) is a scatter diagram of the turbidity and the pH value, and FIG.(b) shows a relation fitting curve of the turbidity and the pH value.
Figure 3A:
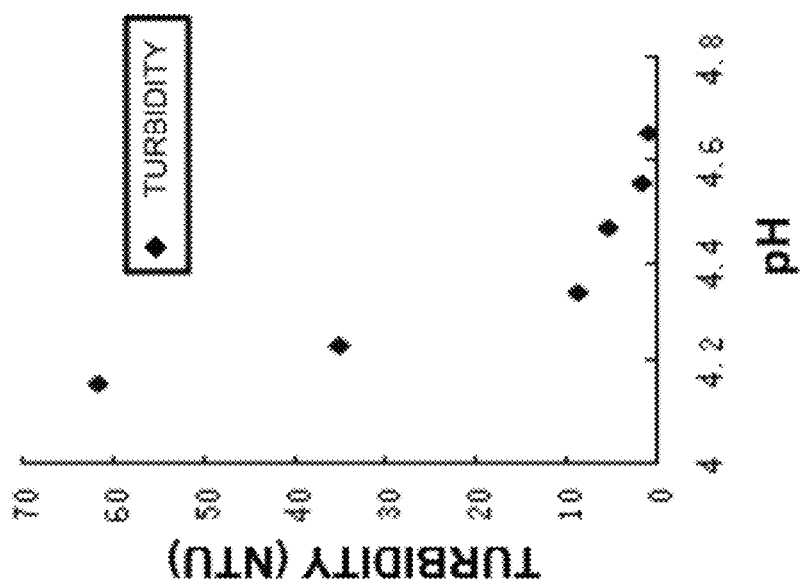

Logarithms of the determined turbidity values are taken with a base of 10, and least square fitting is performed on the log values and the pH values, as shown in FIG. 3, to obtain the coefficients in equation $lgN=-npH+lgK$:

free sucrose buffer coefficient n=4.1144 constant lgK=18.915 correlation coefficient 0.9844, which is higher than 0.98.

That is, $lgN=-4.1144pH+18.915$(c)

The Equation (c) is transformed to obtain:

$N=10e(-4.1144 \times pH+18.915)$ (d)

Below, the turbidity point pp is calculated with a tangent method and a secant method respectively.

Example 1 of Tangent Method

Both sides of Equation (d) are derived against pH, to obtain:

$dN/dpH=-4.1144 \times 10e(-4.1144 \times pH+18.915)$ (e)

if $dN/dpH=-11.4$ $-4.1144 \times 10e(-4.1144 \times pH+18.915)=-11.4$(f)

Equation (f) is solved, to obtain: pH=4.5775

Thus, the turbidity point of iron sucrose is calculated: PP=4.5775

Example 2 of Tangent Method $dN/dpH=-4.1144 \times 10e(-4.1144 \times pH+18.915)$ (e)

if $dN/dpH=-20$ $-4.1144 \times 10e(-4.1144 \times pH+18.915)=-20$(g)

Equation (g) is solved, to obtain: pH=4.5182

Thus, the turbidity point of iron sucrose is obtained: PP=4.5182

Example 1 of Secant Method $N=10e(-4.1144 \times pH+18.915)$ (d)

if N=1, $0e(-4.1144 \times pH+18.915)=1$(h)

Equation (h) is solved, to obtain pH=4.5970

Thus, the turbidity point of iron sucrose is obtained: PP=4.5970

Example 2 of Secant Method $N=10e(-4.1144 \times pH+18.915)$ (d)

if N=2, $10e(-4.1144 \times pH+18.915)=2$(i)

Equation (i) is solved, to obtain pH=4.5243

Thus, the turbidity point of iron sucrose is obtained: PP=4.5243

Embodiment 2 Safety Evaluation of Iron Sucrose Through the Turbidity Point PP and Free Sucrose Buffer Coefficient n 1) Test Medicine Name: iron sucrose, samples of different batches available from Nanjing Lifenergy R&D Co., Ltd.

Solvent: 0.9% saline, available from Shandong Hualu Pharmaceutical Co., Ltd, batch No.: A08120904

Formulation method: dissolving iron sucrose in 0.9% saline, to form a solution of desired concentration for test immediately before use (in dark).

Method in Embodiment 1 is used for determining the turbidity point PP and the free sucrose buffer coefficient n 2) Test Animals Source: mice, ICR species, weight 18-22 g, conventional, available from Nanjing Jiangning Qinglongshan Animal breeding Farm.

Weight: 18-22 g
Sex: female to male 1:1
Fasting time: intravenous injection after 4-hour fasting
Number of animals in each group: 10

3) Test Conditions and Method

Laboratory conditions: room temperature 18-22° C., relative humidity 60-70% 4) Test Method and Results The mice are intravenously injected with iron sucrose.
Dose: 245.00 mg Fe/Kg Administration volume and frequency: volume 0.25 ml/10 g, once per day, and administration rate: lower than 10 mg Fe/0.5 ml/min. The 3-day survival rate of the test animals is observed after administration.

5) Experimental Results

TABLE 2

Correlated data of turbidity point (PP), and free sucrose buffer coefficient (n) of iron sucrose and survival rate of test mice

| Test Serial No. | Turbidity point (PP) | Free sucrose buffer Coefficient (n) | Number of 3-day Survived Test animals | 3-day Survival Rate of Test animals |
|---|---|---|---|---|
| 1 | 6.4 | 1.87 | 0 | 0% |
| 2 | 6.0 | 2.20 | 1 | 10% |
| 3 | 5.4 | 2.50 | 5 | 50% |
| 4 | 5.2 | 4.23 | 6 | 60% |
| 5 | 5.0 | 4.05 | 6 | 60% |
| 6 | 4.7 | 4.89 | 8 | 80% |
| 7 | 4.7 | 4.59 | 7 | 70% |
| 8 | 4.6 | 5.28 | 8 | 80% |
| 9 | 4.3 | 5.17 | 7 | 70% |

(in Table 2, turbidity point has two significant figures retained, and n has three significant figures retained)

The turbidity point of iron sucrose and the 3-day survival rate of test animals have significant negative correlation. At the same dose, the higher the turbidity point of the test group is, the lower the 3-day survival rate of the test animals is. In comparison of test groups with similar turbidity points, the higher the free sucrose buffer coefficient n of the test group is, the higher the survival rate of the test animals is, which obviously correlates to the higher buffering capability against the influence of external factors, and the coefficient n should be at least 2.5 or above, i.e., the median lethal threshold.

Embodiment 3

The products of different batches available from Nanjing Lifenergy R&D Co., Ltd were formulated into solutions having a concentration of 20 mg/mL based on the weight of iron, and adjusted to pH 10.80. 10 mL solution with the adjusted pH value was weighted exactly, and 0.1 N hydrochloric acid solution was added with stirring, till the pH value of the solution reached 4.60, and the volume of hydrochloric acid consumed was recorded in Data Table 3.

DATA TABLE 3

Volume of hydrochloric acid consumed

| Serial No. | Turbidity point (PP) | Free Sucrose Buffer Coefficient (n) | Initial pH | Consumption of 0.1N Hydrochloric acid/mL (20 mg/mL) Solution | End-point pH |
|---|---|---|---|---|---|
| 1 | 6.4 | 1.87 | 10.80 | 0.77 | 4.60 |
| 2 | 6.0 | 2.20 | 10.80 | 0.81 | 4.60 |
| 3 | 5.4 | 2.48 | 10.80 | 0.92 | 4.60 |
| 4 | 5.2 | 4.23 | 10.80 | 1.03 | 4.60 |
| 5 | 5.0 | 4.05 | 10.80 | 0.99 | 4.60 |
| 6 | 4.7 | 4.89 | 10.80 | 1.21 | 4.60 |
| 7 | 4.7 | 4.59 | 10.80 | 1.15 | 4.60 |
| 8 | 4.6 | 5.28 | 10.80 | 1.38 | 4.60 |
| 9 | 4.3 | 5.17 | 10.80 | 1.30 | 4.60 |

It can be seen that, after the pH value of 20 mg/mL iron sucrose solution is decreased from 10.80 to 4.60, the consumption of 0.1 N hydrochloric acid solution is positive correlated to the free sucrose buffer coefficient n, and the consumption of 0.1 N hydrochloric acid of iron sucrose of the batches with a high free sucrose buffer coefficient n is high. That is to say, the iron sucrose solution with a high free sucrose buffer coefficient n is more tolerant to external influential factors such as hydrochloric acid. At the same amount of hydrochloric acid added, the iron sucrose solution with a higher free sucrose buffer coefficient n is less likely to have insoluble ingredients occurred, thus having a higher and more stable buffering capability, and accordingly, having a higher safety coefficient.

What is claimed is:

1. A method for determining a turbidity point and a free carbohydrate buffer coefficient of an iron-carbohydrate complex, comprising:
   (1) contacting the iron-carbohydrate complex with an acid such that the iron-carbohydrate complex has an acid degradation;
   (2) determining hydrogen ion concentrations and solution turbidities of the iron-carbohydrate complex in the acid degradation to obtain data of the determined hydrogen ion concentrations and the determined solution turbidities; and
   (3) mathematically fitting the data, to obtain the turbidity point and the free carbohydrate buffer coefficient of the iron-carbohydrate complex through mathematical treatment.

2. The method according to claim 1,
   wherein the step (2) is performed by determining the hydrogen ion concentrations and the solution turbidities at finite points with a pH meter and a turbidimeter, respectively;
   wherein the step (3) is performed by fitting the data in an equation of $\log_m N = n\log_m[H^+] + \log_m K$, and treating the fitted equation with a secant method or a tangent method, to obtain the turbidity point and the free carbohydrate buffer coefficient of the iron-carbohydrate complex; and
   wherein N represents the determined solution turbidities, $[H^+]$ represents the determined hydrogen ion concentrations, m is a number greater than zero and not equal to 1, and n and K are coefficients obtained by the fitting and treating of the equation.

3. The method according to claim 2, wherein m is 10 such that the equation is $\lg N = npH + \lg K$, pH is a pH value of the iron-carbohydrate complex in the acid degradation, and step (3) comprises
   performing least square fitting on the log values and the corresponding pH values.

4. The method according to claim 2, wherein as for the tangent method, different tangent slopes in a tangent slope range from −30 to 0 is selected.

5. The method according to claim 4, wherein the tangent slope range is from −20 to −5.

6. The method according to claim 2, wherein as for the secant method, different secant iteration distances in an iteration distance range such that the turbidity of the solution is higher than 0 and lower than 5 is selected.

7. The method according to claim 6, wherein the iteration distance range comprises a range in which the solution turbidity is higher than 0.5 and lower than 3.

8. The method according to claim 1, wherein the carbohydrate in the iron-carbohydrate complex comprises at least one selected dextran, dextrin, gluconate, sorbitol, or sucrose, with sucrose being preferred.

9. The method according to claim 1, wherein the acid is at least one selected from hydrochloric acid, sulfuric acid, nitric acid, perchloric acid, hydrobromic acid, hydroiodic acid, hyperbromic acid, chloric acid, bromic acid, permanganic acid, hydroboric acid, fluorosulfonic acid, cyanic acid, thiocyanic acid, trifluoroacetic acid, trichloroacetic acid, methanesulfonic acid, benzenesulfonic acid, oxalic acid, and formic acid, with hydrochloric acid being preferred.

10. A method of safety evaluation of an iron-carbohydrate complex, comprising:
   (1) contacting the iron-carbohydrate complex with an acid such that the iron-carbohydrate complex has an acid degradation;
   (2) determining hydrogen ion concentrations and solution turbidities of the iron-carbohydrate complex in the acid degradation to obtain data of the determined hydrogen ion concentrations and the determined solution turbidities; and
   (3) mathematically fitting the data, to obtain the turbidity point and the free carbohydrate buffer coefficient of the iron-carbohydrate complex through mathematical treatment.

11. The method according to claim 10,
   wherein the step (2) is performed by determining the hydrogen ion concentrations and the solution turbidities at finite points with a pH meter and a turbidimeter, respectively;
   wherein the step (3) is performed by fitting the data in an equation of $\log_m N = n\log_m[H^+] + \log_m K$, and treating the fitted equation with a secant method or a tangent method, to obtain the turbidity point and the free carbohydrate buffer coefficient of the iron-carbohydrate complex;
   wherein N represents the determined solution turbidities, [$H^+$] represents the determined hydrogen ion concentrations, m is a number greater than zero and not equal to 1, and n and K are coefficients determined by the fitting and treating of the equation; and
   wherein if the obtained turbidity point is in the range of 4.4-5.3, and the obtained free carbohydrate buffer coefficient n is higher than 2.5, it is indicated that the iron-carbohydrate complex has good safety.

12. The method according to claim 11, wherein m is 10 such that the equation is $\lg N = npH + \lg K$, pH is a pH value of the iron-carbohydrate complex in the acid degradation, and step (3) comprises
   performing least square fitting on the log values and the corresponding pH values.

13. The method according to claim 11, wherein in the tangent method, different tangent slopes in a tangent slope range from −30 to 0, and preferably from −20 to −5 are selected.

14. The method according to claim 11, wherein in the secant method, different secant iteration distances in an iteration distance range such that the solution turbidity is higher than 0 and lower than 5, and preferably higher than 0.5 and lower than 3 are selected.

* * * * *